(12) United States Patent
Mondet

(10) Patent No.: US 6,180,123 B1
(45) Date of Patent: Jan. 30, 2001

(54) COMPOSITION FOR TOPICAL APPLICATION COMPRISING AN OLEFIN COPOLYMER OF CONTROLLED CRYSTALLIZATION AND USE OF SUCH A COPOLYMER IN THE MANUFACTURE OF COMPOSITIONS FOR TOPICAL APPLICATION

(75) Inventor: Jean Mondet, Aulnay-Sous-Bois (FR)

(73) Assignee: L'Oreal, Paris (FR)

( * ) Notice: Under 35 U.S.C. 154(b), the term of this patent shall be extended for 0 days.

(21) Appl. No.: 09/295,414

(22) Filed: Apr. 21, 1999

(30) Foreign Application Priority Data

Apr. 21, 1998 (FR) .................................................. 98 04950

(51) Int. Cl.⁷ ............................ A61K 7/00; A61K 7/025; A61K 7/027; A61K 7/031
(52) U.S. Cl. ........................... 424/401; 424/64; 424/70.7; 424/78.08; 514/844
(58) Field of Search ............................................... 424/401

(56) References Cited

U.S. PATENT DOCUMENTS 5,695,772   12/1997   Kanga et al. ......................... 424/401
5,932,197 * 8/1999   Arnaud ................................... 424/64
5,945,095 * 8/1999   Mougin et al. .................... 424/78.02

FOREIGN PATENT DOCUMENTS 0 081 787   6/1983   (EP) .
0 270 339   6/1988   (EP) .
0 665 008   8/1995   (EP) .

OTHER PUBLICATIONS

T. Imai et al, Chemical Abstracts, 123:152608, Jun. 13, 1995, XP002091759.

H. Starkweather Jr. et al, "Crystalline Order in Copolymers of Ethylene and Propylene", *Macromolecules*, vol. 15, 1982, pp. 1600–1604, XP002091758.

* cited by examiner

*Primary Examiner*—Shelley A. Dodson
*Assistant Examiner*—Konata M. George
(74) *Attorney, Agent, or Firm*—Oblon, Spivak, McClelland, Maier & Neustadt, P.C.

(57) ABSTRACT

A composition for application to keratinous substances, comprising:

a liquid fatty phase and an effective amount of at least one copolymer which is soluble or dispersible in the liquid fatty phase which is selected from crystalline olefin copolymers having a degree of crystallinity of at most 50%.

47 Claims, No Drawings

COMPOSITION FOR TOPICAL APPLICATION COMPRISING AN OLEFIN COPOLYMER OF CONTROLLED CRYSTALLIZATION AND USE OF SUCH A COPOLYMER IN THE MANUFACTURE OF COMPOSITIONS FOR TOPICAL APPLICATION

BACKGROUND OF THE INVENTION

1. Field of the Invention

The present invention relates to a composition comprising at least one olefin copolymer, which is soluble or dispersible in a fatty phase, and which is useful, in particular, for the cosmetic, dermatological, pharmaceutical and hygiene fields. More especially, the invention relates to a composition for the care and/or make-up of the skin, both of the human face and of the human body, the mucous membranes such as the lips and the inside of the lower eyelids, or the superficial body growths such as the eyelashes, eyebrows, nails and hair.

The composition of the invention as a product can be provided, in particular, in the form of a stick or a dish, such as lipsticks or lip balms, cast foundations, products for combating rings under the eyes, eyeshadows or face powders, in the form of a paste or cream which is more or less fluid such as liquid foundations, liquid lipsticks, eyeliners, make-up for the body, sun protection or skin coloring compositions, or mascaras, or in the form of free or compacted powders.

2. Description of the Background

Products for the make up or care of the skin or lips of human beings, such as foundations or lipsticks, generally comprise fatty phases such as waxes and oils, pigments and/or fillers and, optionally, additives, such as cosmetic or dermatological active principles. They can also comprise so-called <<pasty>> products, which have a supple consistency, which make it possible to prepare colored or colorless pastes which can be applied with a brush.

The use of waxes in formulations presents certain disadvantages. In particular, the degree of crystallinity of these waxes is difficult to control and the crystallites present are large in size. Consequently, the use of such waxes in compositions for application to keratinous substances such as the skin, lips and superficial body growths, in particular in cosmetic compositions, results in the applied compositions, and consequently the film applied, becoming matte in appearance.

To overcome this problem, attempts have been made to use conventional polyolefins in place of waxes in cosmetic formulations. Here again, however, the degree of crystallinity is too high and is difficult to control. In addition, the size and the morphology of the crystallites, predominantly of spherulite type, are harmful to the production of compositions having the desired cosmetic properties, in particular of gloss.

Patent Application JP 65809 (assigned to the Company Shiseido), describes lipstick compositions comprising a siloxysilicate resin (with a three-dimensional network), a volatile silicone oil with a cyclic silicone chain and pulverulent fillers. Likewise, JP 62-61911, assigned to the Company Noevier, discloses lipstick, eyeliner and foundation compositions comprising one or more hydrocarbon-comprising waxes. WO 97/17362, assigned to Revlon, also discloses semimatte cosmetic compositions comprising a volatile solvent and an organosiloxane polymer emulsifier comprising at least one hydrophilic radical or portion and at least one lipophilic radical or portion.

These compositions have the disadvantage of leaving on the lips, after evaporation of the silicone oils, a film which becomes uncomfortable over time, i.e. a feeling of dryness and of tautness is experienced, dissuading some women from using this type of lipstick.

WO 96/36323, assigned to Procter & Gamble, discloses mascara compositions of the water-in-oil emulsion type, which exhibit good hold and which exhibit resistance to water. These compositions comprise, inter alia, a water-insoluble polymer, generally known as a latex, in combination with a surfactant of the alkyl- or alkoxydimethicone copolyol type, hydrocarbon-comprising oils, pigments and fillers, as well as waxes.

WO-A-96/10642, assigned to Revlon, discloses a glossy cosmetic composition comprising a polymer, which is an adhesive at room temperature, a volatile solvent, a non-volatile oil and a particulate dry material. The adhesive polymers are selected from polymers having a vinyl, methacrylic or acrylic backbone and pendant siloxane and fluorinated groups, polymers having a vinyl, methacrylic or acrylic backbone and pendant siloxane groups, and block or grafted vinylsilicone copolymers.

In addition, EP 0 497 144 and FR 2,357,244 disclose compositions comprising a styrene-ethylene-propylene block copolymer in combination with waxes, light or volatile oils and pigments. These compositions exhibit the disadvantage of not being very comfortable, of having indifferent cosmetic properties and of being difficult to formulate.

The need, therefore, remains for a composition which does not exhibit the above disadvantages and which has a more or less glossy appearance, depending on the wish of the consumer, which does not dry, over time, the skin or the lips on which it is applied and which does not cause discomfort.

SUMMARY OF THE INVENTION

Accordingly, one object of the invention is to provide at least one olefin copolymer of controlled and moderate crystallization, which is soluble or dispersible in a fatty phase, in a cosmetic, dermatological, pharmaceutical or hygienic composition and, more pleasantly, a physiologically acceptable composition, which makes it possible to obtain a film of very good hold which is resistant to water while being very pleasant to apply and to wear throughout the day.

Another object of the invention is to provide such a polyolefin containing composition which, upon application, is supple, flexible and non-sticky.

Briefly, this object and other objects of the present invention as hereinafter will become more readily apparent can be attained by a composition for application to keratinous substances, comprising a liquid fatty phase and an effective amount of at least one copolymer which is soluble or dispersible in the liquid fatty phase which is selected from crystalline olefin copolymers having a degree of crystallinity of at most 50%.

DETAILED DESCRIPTION OF THE PREFERRED EMBODIMENTS

The present crystalline olefin copolymers having controlled and moderate crystallization exhibit crystallites having a specific size and specific morphology. They comprise few or no crystallites of the spherulite type with large dimensions but, in contrast, mainly crystallites of lamellar or the fringed micelle type with small dimensions. The crystallites preferably have a dimension of 1 μm or less, preferably less than 500 nm.

The present invention is, therefore, directed to a composition for application to keratinous substances comprising a liquid fatty phase, which comprises an effective amount and in particular at least 2% by weight, with respect to the total weight of the composition, of at least one crystalline olefin copolymer having a degree of crystallinity at most equal to 50% which is soluble or dispersible in the liquid fatty phase.

This composition is in particular a cosmetic, dermatological, hygiene or pharmaceutical composition. It, therefore, comprises ingredients which are compatible with the skin, mucous membranes and superficial body growths and more especially keratinous fibers.

This composition preferably comprises, in addition, at least one coloring material. Another subject-matter of the invention is a composition which is provided in the form of a cast product and which comprises at least one cosmetic, dermatological, hygienic or pharmaceutical liquid fatty phase and optionally at least one wax which is solid at room temperature, characterized in that it additionally comprises an effective amount and better still at least 2% by weight, with respect to the total weight of the composition, of at least one crystalline olefin copolymer having a degree of crystallinity at most equal to 50% which is soluble or dispersible in the liquid fatty phase.

The present composition can additionally comprise ingredients which are compatible with the skin, mucous membranes and superficial body growths and more especially keratinous fibers, in particular at least one coloring material.

The olefin copolymer is present in an amount which is particularly effective in or is sufficient for producing a film with good hold and/or which is glossy and/or which is resistant to water. The crystalline olefin copolymer or copolymers of the invention can be any olefin copolymer, namely a copolymer comprising solely olefin units, having a controlled and moderate crystalline nature, that is to say a degree of crystallinity at most equal to 50%, preferably of 5–40% and most preferably 10–35%.

These copolymers are generally elastomers and can be synthesized by any known process, particularly by radical initiated polymerization, by Ziegler-Natta catalysis or by metallocene catalysis, preferably by metallocene catalysis.

The copolymers of the invention are solids (waxes or pastes) at room temperature (25° C.).

The copolymerization can be carried out in bulk, in solution or in dispersion.

The crystalline olefin copolymers which are suitable in the present invention have a melting point of less than 150° C., preferably ≦110° C.

The crystalline olefin copolymers of the invention preferably have a weight-average molecular weight $\underline{Mw}$ of ≧30000, more preferably ≧40000 and a polydispersity index $\underline{Mw/Mn}$≦3.5, more preferably ≦2.5, where $\underline{Mn}$ is the number average molecular weight.

The degree of crystallinity of the copolymers is determined, as is well-known, by differential scanning calorimetry (DSC) or by X-ray diffraction, for low degrees of crystallinity.

The preferred olefin copolymers of the invention include the olefin copolymers obtained by metallocene catalysis. Metallocene catalysis allows control of the copolymer properties relating to crystallinity, polymer chain length and distribution homogeneity of the units in the polymer chains. This catalysis allows polymer chains of dense compositions and almost the same lengths to be obtained.

This synthetic route makes possible very good control of the molecular weights of the copolymers and results in polymers of low polydispersity (Polydispersity index≦2). It makes possible very good control of the incorporation of the comonomer in the polymer chains, which are very similar in chemical composition. For this reason, a very good control of the crystallinity is obtained, that is to say of the degree of crystallinity, of its reproducibility and of the nature and size of the crystallites formed.

For further details with regard to the advantages of this synthesis by metallocene catalysis, reference is made to the articles: *Emerging Technologies in Polymer Science and Engineering,* M. P. Zamora et al., *Plastics Engineering,* May 97, pages 75–79, and *Classification of Homogeneous Ethylene-Octene Copolymers Based on Comonomer Content,* S. Bensason et al., *Journal of Polymer Science,* Part B: *Polymer* Physics, Vol. 34, 130–1315 (1996).

In the olefin copolymers of the present invention, the crystalline structure varies according to the level of amorphous comonomer in the copolymer.

Thus, in the case of ethylene/octene copolymers, as described in the article by S. Bensason mentioned above, when the octene content increases, the following changes occur:

for a content of octene≦2.5 mol. %, a change to well-marked crystalline structures with the presence of spherulites, structures of lamellar type known as Type IV, and copolymers then exhibiting degrees of crystallinity of greater than 50%, occur;

for octene contents of the order of 3 mol. %, a change to structures which are still highly crystalline and lamellar but with smaller spherulites (structure of Type III) and copolymers having a degree of crystallinity of 38–50%, occur;

then, for octene contents of 5–6 mol. %, a change to less crystalline structures with very few spherulites and a mixture of structures as lamellae with "fringed micelles" (structure of Type II) and copolymers having a degree of crystallinity of 28–38%, occur;

and, finally, for octene contents of 8–14 mol. %, a change to even more weakly crystalline structures which no longer comprise spherulites or lamellae but solely <<fringed micelles>> (structure of Type I) and copolymers having a degree of crystallinity of 10–28%, occur.

The copolymers recommended for the present invention are those having structures of Types I and II.

The excessively crystalline copolymers with a structure of Type IV are not suitable for the present invention.

The copolymer can be selected according to its properties and according to the subsequent application desired for the composition.

Thus, the polymer may or may not be able to form a film.

Another aspect of the invention is a composition as defined above comprising a volatile liquid fatty phase and comprising at least one active principle selected from cosmetic, dermatological, hygienic or pharmaceutically active principles.

The phrase "volatile fatty phase" is understood to mean any non-aqueous medium which can be evaporated from the skin or lips in less than one hour.

The volatile fatty phase comprises, in particular, oils or solvents having a non-zero vapor pressure at room temperature (20–25° C.) and atmospheric pressure, ranging from $10^{-3}$ to 300 mm of Hg. Oil is understood to mean any non-aqueous substance which is liquid at room temperature and atmospheric pressure.

Another aspect of the invention is the use, in or for the manufacture of a composition in the form of a cast product comprising at least one cosmetic, dermatological, hygienic or pharmaceutical liquid fatty phase and at least one wax, in particular one which is solid at room temperature, of a crystalline olefin copolymer having a degree of crystallinity at most equal to 50% and which is soluble or dispersible in the liquid fatty phase, which copolymer is present in an effective amount and in particular at least 2% by weight, with respect to the total weight of the composition, in order to prepare a film with good hold and/or which is glossy and/or which is resistant to water and/or to decrease, indeed eliminate, the transfer of the film deposited on the mucous membranes such as the lips, and/or on the skin.

Another aspect of the invention is the use, in or for the manufacture of a composition for application to keratinous substances comprising a liquid fatty phase and at least one ingredient selected from cosmetic, dermatological, hygienic and pharmaceutical active principles, coloring materials and their mixtures, of at least one crystalline olefin copolymer having a degree of crystallinity at most equal to 50% and which is soluble or dispersible in the liquid fatty phase, which copolymer is present, in particular, in an effective amount and, in particular, in an amount of at least 2% by weight with respect to the total weight of the composition, for producing a film having good hold and/or which is glossy and/or which is resistant to water deposited on the skin and/or mucous membranes such as the lips.

Still another aspect of the invention is a process for the cosmetic care of or for making up the lips or the skin which consists in applying, to the lips or the skin respectively, a cosmetic composition as defined above.

The copolymer can be dissolved in the fatty phase of the composition by heating the composition above the melting point of the copolymer.

The copolymer is advantageously provided in the form of particles which are dispersed and stabilized at the surface by at least one stabilizing agent.

One advantage of the use of a dispersion of particles in the composition of the invention is that the particles remain in the form of individual particles, without forming agglomerates, in the fatty phase, which would not be the case with inorganic particles of nanometric size. Another advantage of the copolymer dispersion is the possibility of obtaining very fluid compositions (on the order of 130 centipoise), even in the presence of a high level of copolymer.

Furthermore, it has been found that the compositions of the invention exhibit the quality of spreading over and of adhering to the skin, semi-mucous membranes or mucous membranes which are particularly advantageous, as well as are smooth and pleasant to the touch. These compositions additionally have the advantage of being easy to remove, in particular, with a conventional make-up removal milk.

A first class of crystalline olefin copolymers which can be used in the compositions of the invention is α-olefin copolymers, in particular of $C_2$–$C_{16}$ α-olefins, preferably $C_2$–$C_{12}$ α-olefins. These copolymers have, in general, a density (d) at room temperature (20–25° C.) of $0.86 \leq d \leq 0.91$, preferably $0.86 \leq d \leq 0.905$. These copolymers are preferably bi- or terpolymers and very particularly bipolymers.

Suitable bipolymers for incorporation into the compositions of the invention include bipolymers of ethylene and a $C_4$–$C_{16}$, preferably $C_4$–$C_{12}$ α-olefin and bipolymers of propylene and a $C_4$–$C_{16}$, preferably $C_4$–$C_{12}$ α-olefin. More preferably, the α-olefin is selected from the group of 1-butene, 1-pentene, 1-hexene, 1-octene, 1-nonene, 1-decene, 1-undecene, 1-dodecene, 3,5,5-trimethyl-1-hexene, 3-methyl-1-pentene and 4-methyl-1-pentene.

Of these monomers 1-butene and 1-octene are particularly preferred. The level of α-olefin in the bipolymer generally ranges from 2–40 mol. %, preferably 3–30 mol. %, more preferably from 4–20 mol. %.

The recommended ethylene-octene bipolymers are plastomers which have an octene content of 5.2–6.2 mol. % and a degree of crystallinity of 28–38% and elastomers which have an octene content of 8–14 mol. % and a degree of crystallinity of 10–28%.

These bipolymers are synthesized by metallocene catalysis, and are sold by the Dow Chemical Company under the tradenames Affinity® (plastomers) and Engage® (elastomers).

Ethylene-butene bipolymers are sold by the Exxon Company under the tradename Exact Resins®.

Suitable terpolymers for use in the invention include terpolymers of ethylene, propylene and $C_4$–$C_{16}$, α-olefins preferably $C_4$–$C_{12}$ α-olefins. In these terpolymers, the contents of $C_4$–$C_{16}$ α-olefin monomers are as shown above and the preferred α-olefins are butene, hexene and octene.

Other suitable copolymers include those α-olefin copolymers those disclosed in EP 081787.

A second class of olefin copolymers, which is suitable for compositions of the invention, includes the copolymers of ethylene, of propylene or of a cycloolefin, in particular the bipolymers.

The cycloolefin content in the copolymers is generally less than 20 mol. %.

Suitable cycloolefins which can be used include cyclobutene, cyclohexene, cyclooctadiene, norbornene, dimethanooctahydronaphthalene (DMON), ethylidenenorbornene, vinylnorbornene and 4-vinylcyclohexene.

The recommended copolymers of this class are the copolymers of ethylene and of norbornene. The norbornene content in these copolymers is generally less than 18 mol. %, in order to exhibit the required crystalline nature, and these copolymers are synthesized by metallocene catalysis.

Suitable ethylene/norbornene copolymers are sold by Mitsui Petrochemical or Mitsui Sekka under the tradename Apel® and by Hoechst-Celanese under the tradename Topas®.

Other recommended ethylene/cycloolefin copolymers are the ethylene/cyclobutene and ethylene/cyclohexene bipolymers having a low cycloolefin content, generally less than 20 mol. %.

A third class of suitable olefin copolymers is composed of olefin copolymers of controlled tacticity, that is, copolymers comprising units of different tacticity. Suitable such copolymers of controlled tacticity include isotactic propylene/atactic propylene and syndiotactic propylene/atactic propylene copolymers. The iso- or syndiotactic units or blocks confer a crystalline nature on the copolymers, while the amorphous atactic units or blocks prevent an excessively high crystallinity of the copolymers and regulate the degree of crystallinity as well as the morphology and the size of the crystallites of the copolymers.

The content of iso- or syndiotactic units, which are the units which confer the crystalline nature to the copolymer is, therefore, predetermined in order to obtain the required percentage of crystallinity ($\leq 50\%$) in the copolymer.

The content of tactic units generally ranges from 10–80 mol. %. However, the content of tactic units preferably is less than 30 mol. %.

These copolymers are synthesized by metallocene catalysis.

A fourth class of suitable olefin copolymers is composed of copolymers of monoolefins and of monomers with (an) ethylenic bond(s), other than the monoolefins, such as dienes, for example, ethylene/butadiene, propylene/butadiene, ethylene/isoprene and propylene/isoprene bipolymers and ethylene/propylene/diene terpolymers, also obtained by metallocene synthesis.

The content of monomer units with (an) ethylenic bond (s), such as dienes, in the copolymer of controlled crystallization generally ranges from 3–20 mol. %.

In order to improve the crystallinity of the copolymer, it is possible optionally to add, to the composition of the invention, additives which hinder crystallization and promote the formation of small crystals. These additives, although used in a small amount, constitute numerous small germination sites uniformly distributed in the bulk of the material. These additives are typically crystals of an organic or inorganic substance.

In the case of an organic additive which has to crystallize, the latter must have a melting point higher than the melting region of the copolymer and should preferably form small crystals.

At a temperature greater than its melting point, this substance is preferably soluble in the mixture of the liquid fatty phase and of molten polymer. Thus, during cooling, the additive, initially dissolved, recrystallizes in the form of numerous small crystals well-distributed in the mixture and then the polymer recrystallizes, giving small crystalline domains because of the presence of the crystals of additives. This is a conventional technique for the recrystallization of polymers.

It is also possible to adjust the degree of crystallization and the size and the morphology of the olefin copolymers of the invention by mixing a first olefin copolymer of the invention with a second crystalline polymer or copolymer partly compatible with the first olefin copolymer. The second polymer or copolymer can be an olefin copolymer of the invention, but with a different degree of crystallinity from that of the first copolymer, including a higher degree of crystallinity than the degree of crystallinity of the olefin copolymers of the invention.

The second crystallizable polymer can also be a polymer which is different in nature, for example, a copolyethylene/vinyl acetate obtained by radical copolymerization or even a crystallizable polyethylene such as those commonly used in the cosmetics field.

For further details with regard to this method of adjustment of the degree of crystallinity, reference is made to the articles entitled: *Elastomeric Blends of Homogeneous Ethylene-octane Copolymers,* S. Bensason et al., *Polymer,* Vol. 38, No. 15, 1997, pages 3913–19, and *Blends of Homogeneous Ethylene/octene Copolymers,* S. Bensason et al., *Polymer,* Vol. 38, No. 14, 1997, pages 3513–20.

The liquid fatty phase in which the copolymer is dispersed can be composed of any cosmetically or dermatologically acceptable oil, normally a physiologically acceptable oil, selected in particular from carbon-comprising, hydrocarbon-comprising, fluorinated and/or silicone oils of mineral, animal, vegetable or synthetic origin, alone or as a mixture, in so far as they form a homogeneous and stable mixture and in so far as they are compatible with the use envisaged.

The term, liquid fatty phase, is understood to mean any non-aqueous medium which is liquid at room temperature, (20–25° C.), and atmospheric pressure.

Mention may thus be made of hydrocarbon-comprising oils such as liquid paraffin or liquid petrolatum, mink oil, turtle oil, soybean oil, perhydrosqualene, sweet almond oil, calophyllum oil, palm oil, grape seed oil, sesame oil, maize oil, parleam oil, arara oil, rapeseed oil, sunflower oil, cotton seed oil, apricot oil, castor oil, avocado oil, jojoba oil, olive oil or cereal germ oil; esters of lanolic acid, of oleic acid, of lauric acid or of stearic acid; fatty esters such as isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, di (2-ethylhexyl) succinate, diisostearyl malate, glyceryl triisostearate or diglyceryl triisostearate; higher fatty acids with at least 12 carbon atoms such as myristic acid, palmitic acid, stearic acid, behenic acid, oleic acid, linoleic acid, linolenic acid or isostearic acid; higher fatty alcohols with at least 12 carbon atoms such as stearyl alcohol or oleyl alcohol, linoleyl or linolenyl alcohol, isostearyl alcohol or octyldodecanol; silicone oils such as polydimethylsiloxanes (PDMS), which are optionally phenylated, such as phenyltrimethicones, phenyltrimethylsiloxydiphenylsiloxanes, diphenylmethyldimethyltrisiloxanes, diphenyldimethicones, phenyldimethicones or polymethylphenylsiloxanes, or which are optionally substituted by aliphatic and/or aromatic groups, which are optionally fluorinated, or by functional groups such as hydroxyl, thiol and/or amine groups; polysiloxanes modified by fatty acids, fatty alcohols or polyoxyalkylenes, fluorinated silicones or perfluorinated oils.

Suitable oils also include the preferred silicone oils, of polydimethylsiloxanes, polymethylphenylsiloxanes, silicones comprising polyoxyalkylene blocks or grafts, in particular polyoxyethylene or copoly(oxyethylene-oxypropylene) blocks or grafts such as dimethicone copolyols, silicones simultaneously carrying hydrophobic hydrocarbon-comprising groups, for example, $C_2$–$C_{30}$ alkyl groups and polyoxyethylenated or copoly(oxyethylenated/oxypropylenated) blocks or grafts such as alkyldimethicone copolyols, or silicones carrying fluorinated or perfluorinated groups such as perfluoroalkylated polydimethylsiloxanes and perfluoroalkylated polymethylphenylsiloxanes.

Other oils, which are acceptable, include one or more oils which are volatile at room temperature. These volatile oils are favorable for the preparation of films having total transfer free properties being obtained. After evaporation of these oils, a supple and non-sticky film-forming deposit is obtained on the skin or mucous membranes which follows the movement of the skin or lips respectively on which the composition is applied. These volatile oils in addition facilitate the application of the composition to the skin, mucous membranes or superficial body growths.

These oils can be hydrocarbon-comprising oils or silicone oils optionally comprising alkyl or alkoxy groups at the end of the silicone chain or pendant alkyl or alkoxy groups.

Suitable volatile silicone oils include linear and cyclic silicones having from 2–7 silicon atoms, these silicone oils optionally comprising alkyl or alkoxy groups having from 1–10 carbon atoms.

Suitable other volatile oils include $C_8$–$C_{16}$ isoparaffins and fluorinated or perfluorinated oils. These volatile oils represent, in particular, from 30–97.99% of the total weight of the composition and better still from 30–75%.

Suitable particular volatile oils include octamethylcyclotetrasiloxane, decamethylcyclopentasiloxane, hexadecamethylcyclohexasiloxane, heptamethylhexyltrisiloxane, heptamethyloctyltrisiloxane and $C_8$–$C_{16}$ isoparaffins such as Isopars, Permethyls and, in particular, isododecane or isohexadecane.

In a specific embodiment of the invention, the liquid fatty phase is selected from the group comprising:

non-aqueous liquid compounds having an overall solubility parameter according to the Hansen solubility space of less than 17 $(MPa)^{1/2}$, monoalcohols having an overall solubility parameter according to the Hansen solubility space of less than or equal to 20 $(MPa)^{1/2}$, or mixtures thereof.

The overall solubility parameter δ according to the Hansen solubility space is defined in *Solubility Parameter Values* by Eric A. Grulke, in the *Polymer Handbook*, 3rd Edition, Chapter VII, pages 519–559, by the relationship:

$$\delta = (d_p^2 + d_D^2 + d_H^2)^{1/2}$$

in which:

$d_p$ characterizes the London dispersion forces resulting from the formation of dipoles induced during molecular impacts, $d_D$ characterizes the forces of Debye interactions between permanent dipoles, and $d_H$ characterizes the forces of specific interactions (hydrogen bonds, acid/base or donor/acceptor type, and the like). The definition of the solvents in the three-dimensional solubility space according to Hansen is described by C. M. Hansen in *The Three-Dimensional Solubility Parameters*, J. Paint Technol., 39, 105 (1967).

Suitable liquid fatty phases having an overall solubility parameter according to the Hansen solubility space of less than or equal to 17 $(Mpa)^{1/2}$ include vegetable oils formed by esters of fatty acids and of polyols, in particular triglycerides, such as sunflower oil, sesame oil and rapeseed oil, and esters derived from long-chain acids and alcohols, that is to say, having from 6–20 carbon atoms, in particular esters of formula RCOOR', in which R represents the residue of a higher fatty acid comprising from 7–19 carbon atoms and R' represents a hydrocarbon-comprising chain comprising from 3–20 carbon atoms such as palmitates, adipates and benzoates, in particular diisopropyl adipate.

Suitable hydrocarbons include, in particular, liquid paraffin, liquid petrolatum, hydrogenated polyisobutylene, isododecane and Isopars, which are volatile isoparaffins.

Also included are silicone oils such as polydimethylsiloxanes and polymethylphenylsiloxanes, which are optionally substituted by aliphatic and/or aromatic groups, which are optionally fluorinated, and by functional groups such as hydroxyl, thiol and/or amine groups, and volatile silicone oils, in particular, volatile cyclic silicone oils.

Solvents are also included, alone or in mixtures and are selected from:

(i) linear, branched and cyclic esters having more than 6 carbon atoms, (ii) ethers having more than 6 carbon atoms, and (iii) ketones having more than 6 carbon atoms.

The term "monoalcohols having an overall volubility parameter according to the Hansen solubility space of less than or equal to 20 $(MPa)^{1/2}$" is understood to mean aliphatic fatty alcohols having at least 6 carbon atoms, the hydrocarbon-comprising chain not comprising a substituent group. Suitable monoalcohols of the invention include oleyl alcohol, decanol, dodecanol, octadecanol and linoleyl alcohol.

It is also possible to employ non-aqueous media such as those described in FR 2,710,646 of L.V.M.H.

The choice of the non-aqueous medium is made according to the nature of the monomers which constitute the copolymer.

Furthermore, the liquid fatty phase in which the copolymer is dissolved or dispersed can represent from 30–97.99% of the total weight of the composition, preferably from 30–75%.

The composition can comprise a coloring material comprising one or more pulverulent compounds and/or one or more fat-soluble dyes, for example, in a proportion of 0.01–70% of the total weight of the composition. The pulverulent compounds can be selected from pigments and/or pearlescent agents and/or fillers commonly used in cosmetic and dermatological compositions. The pulverulent compounds can represent from 0.1–98% of the total weight of the composition, preferably from 1–80%. The smaller the amount of pulverulent compounds, the better the comfort qualities. Consequently, these pulverulent compounds preferably represent from 0.1–40%, more preferably from 1–30%.

In practice, the copolymer can represent up to 60%, as active material or dry matter, of the total weight of the composition, preferably 12–60% by weight.

Preferably, the pigment(s)/copolymer ratio by weight is <1, preferably ≦0.9, more preferably ≦0.5. This ratio can fall to 0.015. The film transfers slightly above 0.5 and the film transfers to a significant extent above 1.

The composition of the invention can advantageously comprise at least 30% by weight of fatty phase with respect to the total weight of the composition. A granular and pulverulent texture is obtained below 30%. This is not very desirable when it is desired to obtain a non-granular homogeneous appearance as a cream, gel or stick.

The pigments may be white or colored and may be inorganic and/or organic. Suitable inorganic pigments include titanium dioxide, optionally treated on its surface, zirconium and cerium oxides, and iron or chromium oxides, manganese violet, ultramarine blue, chromium hydrate and ferric blue. Suitable organic pigments include carbon black, pigments of D&C type and lakes based on cochineal carmine or on barium, strontium, calcium and aluminum.

The pearlescent pigments may be selected from white pearlescent pigments such as mica covered with titanium oxide or with bismuth oxychloride, colored pearlescent pigments, such as titanium oxide-coated mica with iron oxides, titanium oxide-coated mica with, in particular, ferric blue or chromium oxide titanium oxide-coated mica with an organic pigment of the abovementioned type, and pearlescent pigments based on bismuth oxychloride.

Suitable fillers may be inorganic or organic and lamellar or spherical, and include talc, mica, silica, kaolin, Nylon powder (Orgasol from Atochem), poly-β-alanine powder, polyethylene powder, Teflon, lauroyllysine, starch, boron nitride, polytetrafluoroethylene polymer powders, hollow microspheres such as Expancel (Nobel Industrie), polytrap (Dow Corning) and silicone resin microbeads (Tospearls from Toshiba, for example), the abovementioned calcium carbonate, magnesium carbonate, hydrated magnesium carbonate, hydroxyapatite, hollow silica microspheres (Silica Beads from Maprecos), glass microcapsules, ceramic microcapsules and metal soaps derived from organic carboxylic acids having from 8–22 carbon atoms, preferably from 12–18 carbon atoms, for example zinc stearate, magnesium stearate, lithium stearate, zinc laurate or magnesium myristate.

The fillers used, in particular, organic fillers of polymeric nature may or may not be crosslinked and can comprise, within the particles, one or more cosmetic, dermatological, hygienic or pharmaceutical active principles which can be released after application of the composition.

The pigments and the fillers may or may not be superficially coated, in particular surface-treated with silicones, amino acids, fluorinated derivatives or any other substance which promotes the dispersion and the compatibility of the pigment in the composition.

The fat-soluble dyes include, for example, Sudan red, DC Red 17, DC Green 6, β-carotene, soybean oil, Sudan brown, DC Yellow 11, DC Violet 2, DC Orange 5 and quinoline yellow. They can represent from 0.01–20% of the weight of the composition, preferably from 0.1–6%.

The copolymer of the composition of the invention makes possible the formation of a film on the skin, lips and/or mucous membranes, forming a network which traps the coloring materials and/or the active principles. Depending on the relative amount of coloring materials used with respect to the amount of stabilized polymer used, it is possible to obtain a more or less glossy film.

Mention may be made, as cosmetic, dermatological, hygienic or pharmaceutical active principles, which can be used in the composition of the invention, of cosmetic oils, moisturizers, vitamins, essential fatty acids, sphingolipids, sunscreening agents, antioxidants, antiacnes, antiinflammatories, tanning agents (in the absence of UV radiation), depigmenting agents, matifying agents and their mixtures. Suitable moisturizing agents include glycerol and poly(glyceryl methacrylate), sodium hyaluronate and esters of polyol and of sugars. These active materials are used in usual amounts, and, in particular, at concentrations of 0.001–20% of the total weight of the composition.

Furthermore, the composition of the invention may comprise, according to the type of application desired, constituents conventionally used in the fields under consideration, which are present in an amount appropriate to the desired pharmaceutical dosage form.

In particular, the composition may comprise, in addition to the liquid fatty phase in which the polymer is stabilized, additional fatty phases which can be selected from waxes, oils, gums and/or pasty fatty substances of vegetable, animal, mineral or synthetic origin, indeed even silicone fatty phases and their mixtures.

Suitable waxes which may be used include those which are solid at room temperature and which can be present in the composition of the invention. Particularly preferred are waxes having a melting point of greater than 45° C., for example, hydrocarbon-comprising waxes such as beeswax, carnauba wax, candelilla wax, ouricury wax, japan wax, coke fibre wax, sugarcane wax, paraffin wax, lignite wax, microcrystalline waxes, lanolin wax, montan wax, ozokerites, polyethylene waxes, the waxes obtained by the Fischer-Tropsch synthesis, hydrogenated oils, or fatty esters and glycerides which are solid at 25° C. Also useful are silicone waxes which include alkylpolymethylsiloxanes, alkoxypolymethylsiloxanes, and/or polymethylsiloxane esters. The waxes can be provided in the form of stable dispersions of colloidal wax particles, such that they can be prepared by known methods such as those described in *Microemulsions Theory and Practice,* edited by L. M. Prince, Academic Press, 1977, pages 21–32. Suitable waxes also include those which are liquid at room temperature such as jojoba oil.

The waxes can be present in an amount of 0–50% by weight in the composition, preferably 10–30%.

The composition may additionally comprise any additive conventionally used in such compositions such as thickeners, fragrances, preservatives, surfactants and fat-soluble polymers such as polyalkylenes, in particular polybutene, polyacrylics and silicone polymers which are compatible with the fatty phase, as well as polyvinylpyrrolidone derivatives. Of course, any one or all of these substances and other possible substances, as well as their amounts, are selected so that the advantageous properties of the composition of the invention are not, or not substantially, detrimentally affected by the inclusion of one or more of the substances.

Suitable thickening agents which may be employed include bentonites, treated silicas, fat-soluble alkylated guar gums, block or grafted polymers comprising at least one block which is soluble in the composition and one insoluble block, such as, for example, polystyrene/copoly(ethylene-propylene) or polystyrene/copoly(ethylene-butylene) bi- or triblock copolymers, poly(vinylpyrrolidone-hexadiene), silicone gums and KSG silicones.

The silicone gums generally have a number average molecular weight of 200,000–1,000,000. Suitable silicone gums, which may be used alone or in the form of a mixture in a solvent, include the following copolymers:

poly[(dimethylsiloxane)/(methylvinylsiloxane)]
poly[(dimethylsiloxane)/(diphenylsiloxane)]
poly[(dimethylsiloxane)/(phenylmethylsiloxane)]
poly[(dimethylsiloxane)/(diphenylsiloxane)/(methylvinylsiloxane)];

and the following mixtures:

the mixtures formed from a polydimethylsiloxane hydroxylated at the chain end and from a cyclic polydimethylsiloxane; and the mixtures formed from a polydimethylsiloxane gum and from a cyclic silicone; and the mixtures of two polydimethylsiloxanes with different viscosities.

The compositions of the invention may additionally comprise fat-soluble homopolymers and copolymers and/or homopolymers and copolymers which are dispersible in the fatty phase, other than the olefin copolymers of controlled crystallization of the invention. Suitable homopolymers and copolymers include polyolefins such as polyethylene, polybutene and polydecene; copolymers of (meth)acrylic amides and/or esters; copolymers of vinyl esters, for example ethylene/vinyl acetate copolymers; vinyl or (meth)acrylic homopolymers or copolymers carrying a silicone group, such as, for example, grafted copolymers with a (meth) acrylic backbone and macromer silicone grafts; copolymers with a (meth)acrylic backbone or blocks and with hydrocarbon-comprising grafts or blocks, for example, polyisobutylene; grafted or block copolymers with a polyorganosiloxane backbone or block and with (meth)acrylic and/or vinyl grafts or blocks; or fluorinated or perfluorinated homopolymers or copolymers, for example, perfluorinated polyethers such as those sold under the name Fomblins®, perfluorinated (meth)acrylic homo- or copolymers, fluorinated vinyl homo- or copolymers, fluorinated olefin homo- or copolymers and fluorinated poly(vinyl ethers).

In a specific embodiment of the invention, the compositions of the invention may be prepared in the usual way by one of skill in the art. The compositions may be provided in the form of a cast product, for example, in the form of a stick or in the form of a dish which may be used by direct contact or with a sponge. In particular, the compositions find an application as cast foundations, cast face powders, cast eyeshadows, lipsticks, bases or balms for caring of the lips, or a product for combating rings under the eyes. They may also be provided in the form of a supple paste with a dynamic viscosity at 25° C. of the order of 1–40 Pa.s, or in the form of a gel or of a cream which is more or less fluid. They may then constitute foundations or lipsticks, anti-sun products or products for coloring the skin. Preferably, the compositions of the invention have a dynamic viscosity $\mu \geqq 5$ Pa.s as measured at 25° C. with an imposed stress rheometer HAAKE RS75 with coneplate geometry (cone characteristic, 20 mm diameter, 1° angle and 40 $\mu$m gap).

The compositions of the invention are advantageously anhydrous and may comprise less than 5% of water with respect to the total weight of the composition. They may then be provided in particular in the form of an oily gel, an oily liquid or oil, a paste or a stick. These pharmaceutical dosage forms are prepared by the usual methods in the fields under consideration.

The compositions of the invention may also advantageously be formulated in the form of a water-in-oil, oil-in-water or water-in-wax emulsion, in which compositions the olefin copolymers of the invention are used to replace all or part of the waxes usually present in these emulsions. In particular, the wax can be composed of at least one olefin copolymer of the invention and of at least one oil, which may or may not be volatile.

The compositions may be prepared in the form of vesicular dispersions comprising ionic and/or nonionic lipids.

These compositions for topical applications can constitute, in particular, a cosmetic, dermatological, hygienic or pharmaceutical composition for protecting, treating or caring for the face, neck, hands or body, for example, anhydrous care cream, anti-sun oil or body gel, a make-up composition, for example, make-up gel, or an artificial tanning composition.

Having now generally described the invention, a further understanding can be obtained by reference to certain specific examples which are provided herein for purpose of illustration only and are not intended to be limiting unless otherwise specified.

EXAMPLES

Example 1

Preparation of a Lipstick Stick

Choice of the polymer:

Copolymer (ethylene/1-octene) with 4.7 mol. % of octene, prepared by metallocene synthesis and sold by Dow Chemical under the name of Engage® CGCT 8817-O (degree of crystallinity: 25%), with the characteristics given by J. Minick, J. in Appl. Polym. Sci., Vol. 58, 1371–84 (1995).

| Composition of the formula: | |
|---|---|
| Polymer | 14 g |
| Lanolin | 7 g |
| Capric/caprylic triglyceride | 13 g |
| Sesame oil | 22 g |
| Cyclopentadimethylsiloxane | 32 g |
| Pigments | 12 g |

All the constituents, except the volatile silicone, are mixed under warm conditions, with heating at 105° C. to dissolve the polymer. After homogenizing and milling the pigments, the volatile silicone is then added at 90° C. and the mixture is cast in a suitable mold.

A stick with good theological characteristics is obtained which deposits a comfortable film after application to the lips.

Example 2

Preparation of a Lipstick

Choice of the polymer:

Copolymer (ethylene/1-octene) prepared by metallocene synthesis, and sold by Dow Chemical under the name Engage® 8400 (degree of crystallinity: 10–35%)

| Composition of the formula: | |
|---|---|
| Polymer Engage ® 8400 | 18 g |
| Pigment (Iron oxides) | 6 g |
| Isododecane | 50 g |
| Parleam oil | 26 g |

All the constituents are mixed under warm conditions and the mixture is cast in a suitable mold.

A stick with good rheological characteristics is obtained which deposits a comfortable film after application to the lips.

The disclosure of French priority Application Number 9804950 filed Apr. 21, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is desired to be secured by letters patent:

1. A composition for application to keratinous substances, comprising:
   a liquid fatty phase and
   an effective amount of at least one copolymer which is solid at room temperature and is soluble or dispersible in the liquid fatty phase which is selected from crystalline olefin copolymers having a degree of crystallinity of at most 50%.

2. The composition according to claim 1, wherein the copolymer is at least 2% by weight of the total weight of the composition.

3. The composition according to claim 1, wherein the copolymer has a weight average molecular weight Mw of $\geqq 30000$.

4. The composition according to claim 3, wherein the copolymer has a polydispersity index Mw/Mn of $\leqq 3.5$, where Mn is the number average molecular weight.

5. The composition according to claim 1, wherein the composition is provided in the form of a cast product comprising a cosmetic, dermatological, hygienic or pharmaceutical liquid fatty phase and at least one solid wax.

6. The composition according to claim 1, which is cast into the form of a film.

7. The composition according to claim 1, wherein the liquid fatty phase is volatile.

8. The composition according to claim 1, which further comprises at least one active principle selected from the group consisting of cosmetic, dermatological, hygienic and pharmaceutical active principles and their mixtures.

9. The composition according to claim 1, which further comprises at least one coloring material.

10. The composition according to claim 1, wherein the olefin copolymer is selected from the group consisting of:
(A) α-olefin copolymers, copolymers of olefins and of cycloolefins, copolymers of α-olefins and of monomers with (an) ethylenic bond(s); and
(B) α-olefin copolymers with tactic and atactic units.

11. The composition according to claim 1, wherein the α-olefin copolymers are selected from the group consisting of bipolymers of ethylene or of propylene and of a $C_4$–$C_{16}$ α-olefin and terpolymers of ethylene, of propylene and of $C_4$–$C_{16}$ α-olefin.

12. The composition according to claim 1, wherein the $C_4$–$C_{16}$ α-olefin is selected from the group consisting of 1-butene, 1-pentene, 1-hexene, 1-heptene, 1-octene, 1-nonene, 1-decene, 1-undecene, 1-dodecene, 3,3,5-trimethyl-1-hexene, 3-methyl-1-pentene and 4-methyl-1-pentene.

13. A The composition according to claim 1, wherein the mol. percentage of α-olefin is at most equal to 40%.

14. The composition according to claim 1, wherein the olefin copolymers are selected from the group consisting of bipolymers of ethylene or of propylene with cyclobutene, cyclohexene, cyclooctadiene, norbornene, dimethanooctahydronaphthalene (DMON), ethylidenenorbornene, vinylnorbornene and 4-vinylcyclohexene and terpolymers of ethylene, of propylene and of cycloolefins.

15. The composition according to claim 1, wherein the copolymer of olefin and of cycloolefin comprises less than 20 mol. % of cycloolefin.

16. The composition according to claim 1, wherein the copolymer of an α-olefin and of a cycloolefin is an ethylene/norbornene copolymer comprising less than 18 mol. % of norbornene.

17. The composition according to claim 1, wherein the copolymers of α-olefin and of monomers with (an) ethylenic bond(s) are selected from the group consisting of ethylene/butadiene and ethylene/isoprene bipolymers.

18. The composition according to claim 17, wherein the bipolymer comprises less than 20 mol. % of monomers with (an) ethylenic bond(s).

19. The composition according to claim 1, wherein the α-olefin copolymers with tactic and atactic units are selected from the group consisting of polypropylenes with isotactic and atactic units and polypropylenes with syndiotactic and atactic units.

20. The composition according to claim 19, wherein the content of tactic units in the copolymers is less than 30 mol. %.

21. The composition according to claim 1, wherein the olefin copolymers are obtained by metallocene synthesis.

22. The composition according to claim 1, in which the composition of the liquid fatty phase is composed of carbon-comprising, hydrocarbon-comprising, fluorinated oils of mineral, animal, vegetable or synthetic origin, and/or silicone oils alone or as a mixture.

23. The composition according to claim 1, in which composition the liquid fatty phase is selected from the group consisting of liquid paraffin or liquid petrolatum, mink oil, turtle oil, soybean oil, perhydrosqualene, sweet almond oil, calophyllum oil, palm oil, parleam oil, grape seed oil, sesame oil, maize oil, rapeseed oil, sunflower oil, cotton seed oil, apricot oil, castor oil, avocado oil, jojoba oil, olive oil or cereal germ oil; esters of lanolic acid, of oleic acid, of lauric acid or of stearic acid; isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, di(2-ethylhexyl) succinate, diisostearyl malate, glyceryl triisostearate or diglyceryl triisostearate; myristic acid, palmitic acid, stearic acid, behenic acid, oleic acid, linoleic acid, linolenic acid or isostearic acid; stearyl alcohol or oleyl alcohol, linoleyl or linolenyl alcohol, isostearyl alcohol or octyldodecanol; phenyltrimethicones, phenyltrimethylsiloxydiphenyl-siloxanes, diphenylmethyldimethyltrisiloxanes, diphenyldimethicones, phenyldimethicones or polymethylphenylsiloxanes, or which are optionally substituted by aliphatic and/or aromatic groups or by functional groups selected from the groups consisting of hydroxyl, thiol and/or amine groups; polysiloxanes modified by fatty acids, fatty alcohols or polyoxyalkylenes, fluorinated silicones or perfluorinated oils; octamethylcyclo-tetrasiloxane, decamethylcyclopentasiloxane, hexadecamethylcyclohexasiloxane, heptamethylhexyltrisiloxane, heptamethyloctyltrisiloxane or $C_8$–$C_{16}$ isoparaffins.

24. The composition according to claim 1, wherein the liquid fatty phase is selected from the group consisting of:
non-aqueous liquid compounds having an overall solubility parameter according to the Hansen solubility space of less than 17 $(MPa)^{1/2}$,
monoalcohols having an overall solubility parameter according to the Hansen solubility space of less than or equal to 20 $(MPa)^{1/2}$,
or mixtures thereof.

25. The composition according to claim 1, wherein the fatty phase comprises at least one oil which is volatile at room temperature.

26. The composition according to claim 1, wherein the fatty phase comprises at least one additional fatty phase selected from the group consisting of waxes, gums and/or pasty fatty substances of vegetable, animal, mineral, synthetic or silicone origin, and their mixtures.

27. The composition according to claim 1, wherein the composition comprises at least one pulverulent compound selected from the group consisting of fillers, pigments, pearlescent agents and their mixtures.

28. The composition according to claim 1, wherein the pulverulent compound and the copolymer are present in a pigment/copolymer ratio of less than 1.

29. The composition according to claim 28, wherein the pulverulent compound represents 0.1–98% of the total weight of the composition.

30. The composition according to claim 29, wherein the pulverulent compound represents from 1–30% of the total weight of the composition.

31. The composition according to claim 29, wherein the olefin copolymer represents, on a dry matter basis, up to 60% of the total weight of the composition.

32. The composition according to claim 31, wherein the olefin copolymer represents, on a dry matter basis, from 12–60% of the total weight of the composition.

33. The composition according to claim 31, wherein the liquid fatty phase comprises at least one oil selected from the group consisting of $C_8$–$C_{16}$ isoparaffins and linear or cyclic silicones having from 2–7 silicon atoms, these silicones optionally comprising alkyl groups having from 1–10 carbon atoms, and their mixtures.

34. The composition according to claim 31, wherein the composition is in the form of a stick; in the form of a supple paste with a dynamic viscosity at 25° C. of the order of 1–40 Pa.s; in the form of a dish; of an oily gel; of an oily liquid; or of a vesicular dispersion comprising ionic and/or nonionic lipids.

35. The composition according to claim 31, wherein the composition is provided in the form of a water-in-oil, oil-in-water or water-in-wax emulsion, said wax optionally composed of a mixture of at least one crystalline olefin copolymer having a degree of crystallinity at most equal to 50% and at least one oil.

36. The composition according to claim 31, which is provided in anhydrous form.

37. A product for the care and/or make-up of the skin, lips and/or eyelashes, comprising:
the composition of claim 1.

38. A cast foundation, a cast face powder, a cast eyeshadow, a lipstick, a base or balm for care of the lips, a product for combating rings under the eyes, a mascara or a make-up for the body, comprising:
the composition of claim 1.

39. A method of treating keratinous substances, comprising:
applying the composition of claim 1 to said keratinous substances.

40. A method of cosmetically treating the skin, comprising:
applying the composition of claim 1 to the skin.

41. The method of claim 39, wherein the crystalline olefin copolymer is selected from the group consisting of:
(A) α-olefin copolymers, copolymers of olefins and of cycloolefins, copolymers of a-olefins and of monomers with (an) ethylenic bond(s); and
(B) α-olefin copolymers with tactic and atactic units.

42. The method of claim 41, wherein the copolymers are selected from the group consisting of bipolymers of ethylene or propylene with a $C_4$–$C_{16}$-α-olefins and terpolymers of ethylene, propylene with $C_4$–$C_{16}$-α-olefins.

43. The method of claim 42, wherein the $C_4$–$C_{16}$ α-olefin is selected from the group consisting of 1-butene, 1-pentene, 1-hexene, 1-heptene, 1-octene, 1-nonene, 1-decene, 1-undecene, 1-dodecene, 3,3,5-trimethyl-1-hexene, 3-methyl-1-pentene and 4-methyl-1-pentene.

44. The method of claim 41, wherein the copolymers of olefin and of cycloolefin are selected from the group consisting of bipolymers of ethylene or propylene with cyclobutene, cyclohexene, cyclooctadiene, norbornene, dimethanooctahydronaphthalene, ethylidenenorbornene, vinylnorbornene and 4-vinylcyclohexene and terpolymers of ethylene, propylene with a cycloolefin.

45. The method of claim 41, wherein the copolymers of α-olefin and a monomer with (an) ethylenic bond(s) are selected from the group consisting of ethylene/butadiene and ethylene/isoprene bipolymers.

46. The method of claim 41, wherein the α-olefin copolymers with tactic and atactic units are selected from the group consisting of polypropylenes with isotactic and atactic units and polypropylenes with syndiotactic and atactic units.

47. The method of claim 39, wherein the olefin copolymer is obtained by metallocene synthesis.

* * * * *